United States Patent [19]
Wu et al.

[11] Patent Number: 6,133,018
[45] Date of Patent: Oct. 17, 2000

[54] ENZYMATIC SYNTHESIS OF CHIRAL AMINES USING -2-AMINO PROPANE AS AMINE DONOR

[75] Inventors: Wei Wu, Wilmington, Del.; Mohit B. Bhatia, Washington, N.J.; Craig M. Lewis, East Windsor, N.J.; Wei Lang, Edison, N.J.; Alice L. Wang, Green Brook, N.J.; George W. Matcham, Bridgewater, N.J.

[73] Assignee: Celgro, Annandale, N.J.

[21] Appl. No.: 09/266,100

[22] Filed: Mar. 10, 1999

Related U.S. Application Data

[63] Continuation-in-part of application No. 09/086,369, May 28, 1998, abandoned
[60] Provisional application No. 60/077,520, Mar. 11, 1998, and provisional application No. 60/048,280, Jun. 2, 1997.

[51] Int. Cl.$^7$ ............................ C12P 13/00; C12P 13/02; C12P 13/04; C12P 13/22; C12P 13/24
[52] U.S. Cl. .......................... 435/280; 435/106; 435/107; 435/108; 435/109; 435/110; 435/111; 435/112; 435/113; 435/114; 435/115; 435/116; 435/128; 435/129
[58] Field of Search ..................................... 435/280, 128, 435/129, 106–116

[56] References Cited

U.S. PATENT DOCUMENTS 5,300,437  4/1994  Stirling et al. .......................... 435/280
5,457,085  10/1995  Seckinger et al. ...................... 504/289

OTHER PUBLICATIONS

Sisler et al., College Chemistry, Chapter 24, pp. 459–460, Macmillan, NY (1963).

Raunio et al., "Effect of 1–hydroxymethyl– and 1–methyl–1–aminoalkanee on enzymatic leucine–1–oxoglutarate transamination" Acta Chem. Scand. 27(3): 985–9 (1973).

Matcham, et al. "Biocatatysis for Chiral Intermediatis: Meeting Commercial and Technical Challenges" Chemical Oggi, Jun. 1996.

*Primary Examiner*—Sandra Saucier
*Attorney, Agent, or Firm*—Mathews, Collins, Shepherd & Gould, P.A.

[57] ABSTRACT

2-Aminopropane is used as the amine donor in the stereoselective synthesis of a chiral amine from a ketone with a transaminase. In a typical embodiment, (S)-1-methoxy-2-aminopropane is prepared by bringing methoxyacetone into contact with a transaminase in the presence of 2-aminopropane as an amine donor until a substantial amount of methoxyacetone is converted to (S)-1-methoxy-2-aminopropane and 2-aminopropane is converted to acetone. In a second embodiment, L-alanine is prepared by bringing pyruvic acid into contact with a transaminase in the presence of 2-aminopropane as an amine donor.

3 Claims, No Drawings

ENZYMATIC SYNTHESIS OF CHIRAL AMINES USING -2-AMINO PROPANE AS AMINE DONOR

CROSS-REFERENCE TO RELATED APPLICATIONS

This claims the benefit of Provisional Application Serial No. 60/077,520 filed Mar. 11, 1998, which is a continuation-in-part of Ser. No. 09/086,369 filed May 28, 1998, now abandoned which, in turn, claims the benefit of Provisional Application Serial No. 60/048,280 filed Jun. 2, 1997.

The present invention relates to improvements in the enzymatic synthesis of chiral compounds containing an amino group; e.g., chiral amines.

U.S. Pat. Nos. 4,950,606, 5,169,780, 5,300,437, and 5,360,724, the disclosures of which are incorporated herein by reference, describe enantiomeric enrichment of chiral amines through the use of an amino acid transaminase. Amino acid transaminases are known pyridoxal phosphate dependent enzymes found in various microorganisms including Pseudomonas, Escherichia, Bacillus, Saccharomyces, Hansenula, Candida, Streptomyces, Aspergillus, and Neurospora. Two amino acid transaminases, EC 2.6.1.18 and EC 2.6.1-19, have been crystallized and characterized by Yonaha et al., *Agric. Biol. Chem.*, 47 (10), 2257–2265 (1983).

U.S. Pat. Nos. 4,950,606, 5,169,780, and 5,300,437 disclose that individual strains of transaminase-containing organisms can be isolated by chemostat culture, that is, culturing in a constant but restricted chemical environment, with an amino acceptor and an amine as the sole nitrogen source. A typical strain thus isolated in the noted patents was characterized (by the American Type Culture Collection) as *Bacillus megaterium*. Normally omega amino acid transaminases metabolize amino acids in which the amino group is on a terminal, achiral (non-chiral) carbon atom and the amine utilized as the nitrogen source in such a chemostat culture can be of the same type, namely achiral amines such as n-octylamine, cyclohexylamine, 1,4-butanediamine, 1,6-hexanediamine, 6-aminohexanoic acid, 4-aminobutyric acid, tyramine, and benzyl amine. It is also reported in the same patents, however, that the amine utilized as the nitrogen source in such chemostat cultures can be a chiral amine such as 2-aminobutane, α-phenethylamine, and 2-amino-4-phenylbutane. Chiral amino acids such as L-lysine, L-ornithine, β-alanine, and taurine also can be used.

In addition to enantiomeric enrichment, U.S. Pat. Nos. 4,950,606, 5,169,780, and 5,300,437 disclose the stereoselective synthesis of one chiral form of an amine by the action of an amino acid transaminase on a ketone of the formula $R^1COR^2$, in which $R^1$ and $R^2$ are different alkyl or aryl groups, in the presence of an amino donor. The amino donors disclosed are similar to the amines used as the nitrogen source in the chemostat cultures; e.g. achiral amines in which the amino group is on a terminal carbon atom, such a propyl amine and benzyl amine, chiral amines in which the amino group is on a terminal carbon atom, such as (S)-2-aminobutane, and chiral amino acids, such as L-alanine and L-aspartic acid.

The present invention is based on the discovery that the achiral amine 2-aminopropane is unexpectedly superior as an amine donor in such transaminase amine syntheses as compared with either achiral amines in which the amino group is on a terminal carbon atom or chiral amines in which the amino group is on a nonterminal carbon atom. The invention thus constitutes the improvement in-the known stereoselective synthesis of a chiral amine in which a ketone is brought into contact with a transaminase in the presence of an amino donor, of utilizing 2-aminopropane as the amine donor.

The term chiral amine is employed herein in its broadest sense. As described in the above-referenced patents, the known stereospecific synthesis can be applied to the preparation of a wide variety of aliphatic and alicyclic compounds of different, and mixed, functional types, characterized only by the presence of a primary amino group bound to a secondary carbon atom which, in addition to a hydrogen atom, carries either (i) a divalent group forming a chiral cyclic structure, or (ii) two substituents (other than hydrogen) differing from each other in structure or chirality.

Divalent groups forming a chiral cyclic structure include for example 2-methylbutane-1,4-diyl, pentane-1,4-diyl, hexane-1,4-diyl, hexane-1,5-diyl, 2-methylpentane-1,5-diyl. Thus the present improvement of utilizing 2-aminopropane as the amine donor can be used in the stereospecific synthesis of 1-amino-2-methylcyclopentane from 2-methylcyclopentanone, 1-amino-3-methylcyclopentane from 3-methylcyclopentanone, 1-amino-2-methylcyclohexane from 2-methylcyclohexanone, etc.

The two different substituents on the secondary carbon atom ($R^1$ and $R^2$ above) also can vary widely and include alkyl, aralkyl, aryl, halo, hydroxy, lower alkyl, lower alkoxy, lower alkylthio, cycloalkyl, carboxy, cabalkoxy, carbamoyl, mono- and di-(lower alkyl) substituted carbamoyl, trifluoromethyl, phenyl, nitro, amino, mono- and di-(lower alkyl) substituted amino, alkylsulfonyl, arylsulfonyl, alkylcarboxamido, arylcarboxamido, etc., as well as alkyl, aralkyl, or aryl substituted by the foregoing.

Thus the present improvement of utilizing 2-aminopropane as the amine donor also can be used in the stereospecific synthesis of 2-aminobutane from butanone, 2-amino-1-butanol from 1-hydroxybutan-2-one, alanine from pyruvic acid, 1-amino-1-phenylethane from acetophenone, 1-amino-1-(2-methoxy-5-fluorophenyl) ethane from 2-methoxy-5-fluoroacetophenone, γ-aminopentanoic acid from levulinic acid, 1-amino-1-phenylpropane from 1-phenypropan-1-one, 1-amino-1-(4-bromophenyl)propane from 1-(4-bromophenyl)propan-1-one, 1-amino-1-(4-nitrophenyl)-propane from 1-(4-nitrophenyl)propan-1-one, 1-phenyl-2-aminopropane from 1-phenylpropan-2-one, valine from 2-oxo-3-methylbutanoic acid, 1-(3-trifluoromethylphenyl)-2-aminopropane from 1-(3-trifluoromethylphenyl)propan-1-one, 2-aminopropanol from hydroxypropanone, 1-methoxy2-aminopropane from methoxyoxypropanone, 1-amino-1-phenylbutane from 1-phenylbutan-1-one, 1-phenyl-2-aminobutane from 1-phenylbutan-2-one, 1-(2,5-dimethoxy-4-methylphenyl)-2-aminobutane from 1-(2,5-dimethoxy-4-methylphenyl) butan-2-one, 1-(4-hydroxyphenyl)-3-aminobutane from 1-(4-hydroxyphenyl)butan-3-one, 1-amino-1-(2-naphthyl) ethane from 2-acetylnaphthalene, phenylalanine from phenylpyruvic acid, glutamic acid from 2-ketoglutaric acid, aspartic acid from 2-ketosuccinic acid, and the like.

In contrast to the amine donors reported in the prior art, and indeed the majority of aminoalkane amino donors which are theoretically available, 2-aminopropane possesses the relatively unique combination of (i) being achiral and (ii) having the amino group on a non-terminal aliphatic carbon atom. Thus notwithstanding the use of an omega-amino acid transaminase, which in nature acts on an amino group in the terminal or ω-position of an amino acid, it has been found that the use as an amino donor having an amino group on a non-terminal aliphatic carbon atom affords a thermodynamic advantage. While not wishing to be bound by any theory, it appears that this improvement is a consequence of the by-product of the enzymatic reaction in such a case being a ketone, as contrasted with the use of an amine donor having an amino group on a terminal carbon atom, such as ethylamine, n-propyl amine, n-octylamine, 1,4-butanediamine, 1,6-hexanediamine, 6-amino-hexanoic acid, 4-aminobutyric acid, tyramine, or benzyl amine which form aldehyde in the presence of an amino acid transaminase reaction. In reactions involving amino acids from ketoacids, the thermodynamic advantage of using isopropylamine as the amino donor results in an equilibrium constant of approximately 1,000. Because this thermodynamic advantage stems from the chemical environment of the reacting carbonyl group, this applies equally to the synthesis of all chiral α-amino acids from their ketoacids, whether natural or unnatural.

Notwithstanding this thermodynamic advantage, the presence of the amino group on a nonterminal aliphatic carbon atom generally results in chirality, as contrasted with substitution on a terminal carbon atom which, necessarily having two hydrogen atoms, precludes chirality. Since the transaminase is stereoselective, the use of a chiral amine donor means that only half of such an amine is available as a donor. From a commercial point of view, this is unacceptable for an amino donor.

Unfortunately, the vast majority of amino(lower)alkanes satisfying the first objective of having an amino group on a non-terminal carbon atom are themselves chiral. Thus limiting consideration to aminoalkanes having no more than 8 carbon atoms, it is estimated that theoretically there are at least 130 possible homologous and isomeric amines in which the amino group is not on a trisubstituted carbon atom (to be an amino donor, the compound must also carries at least one available hydrogen atom on the carbon atom to which the amino group is bound). Of these 130 possible amino donors, less than half (54) have an amino group on a non-terminal carbon atom and of these, 93% (50) are chiral. Only 4 of the alkyl amines having an amino group on a non-terminal carbon atom are achiral and of these, 3 are prohibitive in terms of cost and availability and again unsuitable as amine donors: 3-aminopentane, 2,2-dimethyl-3-aminopentane, and 4-aminoheptane. Thus of all amino (lower)alkanes theoretically suitable as amino donors, only 2-aminopropane (i) has an amino group on a terminal carbon atom and thus thermodynamically favored over aminoalkanes in which the amino group is on a terminal carbon atom, (ii) is achiral so as to be completely available for reaction, and (iii) is acceptable in terms of cost and availability. As a further advantage, 2-aminopropane also generates a byproduct, acetone, which is readily recoverable and itself an article of commerce.

The actual enzymatic conversion can be effected by conventional culturing techniques with isolated but non-growing cells, or with a soluble amino acid transaminase preparation. The amino acid transaminase can be in free form, either as a cell free extract or a whole cell preparation, or immobilized on a suitable support or matrix such as cross-linked dextran or agarose, silica, polyamide, or cellulose. It also can be encapsulated in polyacrylamide, alginates, fibers, or the like. Methods for such immobilization are described in the literature (see, for example, *Methods of Enzymology*, 44,1976).

Although not necessary, it generally is advantageous to add a source of pyridoxamine such as pyridoxal phosphate.

EXAMPLE 1

The invention can be exemplified by the preparation of (S)-1-methoxy-2-aminopropane, a chemical intermediate for the synthesis of agricultural chemicals, in which methoxyacetone is brought into contact with a transaminase in the presence of 2-aminopropane as an amine donor, permitting the reaction to continue until a substantial amount of methoxyacetone is converted to (S)-1-methoxy-2-aminopropane (and 2-aminopropane is simultaneously converted to acetone), and isolating the (S)1-methoxy-2-aminopropane thus formed. The overall enzymatic transformation can be depicted as follows:

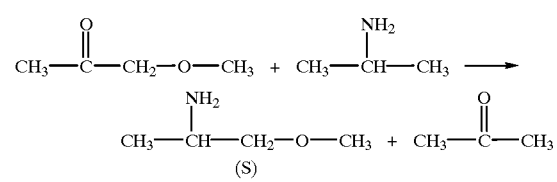

Five millimoles of monobasic sodium phosphate and 250 mL of concentrated hydrochloric acid were added to 1000 mL of water. The mixture was chilled to 5–10° C. in an ice-water bath and 258 mL of 2-aminopropane were added, followed by 206 mL of methoxyacetone (98%). This mixture was mixed and the pH adjusted to 7.5 with either sodium hydroxide or hydrochloric acid, as necessary. The mixture was transferred to a 3 L round bottom reactor with temperature control and agitation apparatus. After the temperature of the reaction mixture was stable at 30±1° C., 0.2 mM of pyridoxal 5'-phosphate was added. The pH is re-adjusted to 7.5 if necessary and a small amount of water may be added to bring the volume of the mixture to 1800 mL.

The enzyme solution was prepared separately. To 200 mL of 5 mM of sodium phosphate solution (pH 7.5), 0.2 mM of pyridoxal 5'-phosphate and 2 g (dry weight) of Bacillus cells, containing an (S)-transaminase were added. When the cells were completely suspended, the enzyme solution was delivered into the reaction mixture described above.

The final reaction broth contained 1.5 M of 2-aminopropane and 1.0M of methoxyacetone. The reaction proceeded for 8 hours at 30±1° C. and pH 7.5, at which point (S)-1-methoxy-2-aminopropane was present in the reaction mixture at a concentration of 0.6M with an ee of greater than 99%.

The reaction was terminated by the addition of 5 mL of concentrated hydrochloric acid, followed by flash distillation to remove unreacted methoxyacetone and the by-product, acetone, in a single cut. A separate column distillation of this distillate late can be conducted subsequently to separate the methoxyacetone and acetone. Two hundred and seventy milliliters of 50% aqueous sodium hydroxide were added to the reaction mixture to deprotonate the amines. The amines were then removed from the mixture by distillation as a single cut and (S)-1-methoxy-2-aminopropane was separated from residual 2-aminopropane by a separate distillation to yield 125 grams of (S)-1-methoxy-2-aminopropane containing 50% water. The product is greater than 99% chemically and enantiomerically pure as determined by gas chromatography analysis.

EXAMPLE 2

The invention can be further exemplified by the synthesis of L-alanine, a useful amino acid, in which pyruvic acid is brought into contact with a transaminase in the presence of 2-aminopropane as an amino donor, permitting the reaction to continue until a substantial amount of pyruvic add is converted to L-alanine and 2-aminopropane is simultaneously converted to acetone. The overall enzymatic transformation can be depicted as follows:

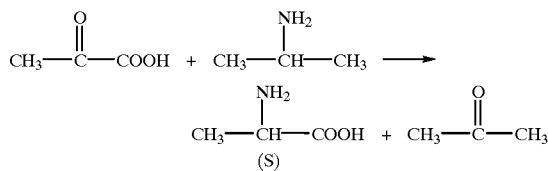

Sodium pyruvate (50 mM, 0.165 g) and isopropylamine hydrochloride (50 mM 0.23 ml of a 6.5 molar solution) were dissolved in 29.0 ml of 50 mM sodium dihydrogen phosphate solution and the pH adjusted to 7.5. Pyridoxal phosphate (1.0 mM, 8.0 mg) was added, followed by 8 mg of E. coli cells containing a (S)-transaminase, so that the final volume was 30 ml and the final pH 7–5. After incubation at 30° C. for 24 hours, the concentrations of isopropylamine, acetone, and L-alanine were measured by HPLC and GC and the L-alanine concentration determined to be 45.6 mM, equivalent to a $K_{eq}$ for the above reaction in excess of 100.

When an analogous reaction was carried out using (R)-transaminase—containing E. coli cells (0.3 g), the conversion proceeded to a D-alanine concentration determined to be 46 mM.

EXAMPLE 3
Synthesis Of L-Alanine

In a separate example of the synthesis of L-alanine, sodium pyruvate (1 M, 110.0 grams) and isopropylamine hydrochloride (1 M, 153 ml of a 6.5 molar solution) were dissolved in 800 ml of 50 mM sodium dihydrogen phosphate buffer and the pH adjusted to 7.5. Pyridoxal phosphate (1 mM, 265 milligrams) was added, followed by 5 grams of E. coli cells containing a (S)-transaminase, so that the final volume was 1 liter and the final pH was 7.5. After incubation at 30° C. for 24 hours, the concentrations of isopropylamine and L-alanine were determined by HPLC and the concentration of acetone by GC. The concentration of produced L-alanine was determined to be 970 mM, equivalent to an equilibrium constant for the reaction of approximately 1000.

EXAMPLE 4
Synthesis Of L-2-Aminobutyric Acid

Sodium ketobutyrate (50 mM, 186 milligrams) and isopropylamine (50 mM, 0.23 ml of a 6.5 molar solution) were dissolved in 29 ml of 50 mM sodium dihydrogen phosphate buffer and the pH adjusted to 7.5. Pyridoxal phosphate (1 mM, 8.0 mg) was added, followed by 100 milligrams of E. coli cells containing a (S)-transaminase, so that the final volume was 30 ml and the final pH was 7.5. After incubation at 30° C. for 24 hours, the concentrations of isopropylamine and L-2-aminobutyric acid were determined by HPLC and the concentration of acetone by G-C. The concentration of produced L-aminobutyric acid was determined to be 48 mM, equivalent to an equilibrium constant for the reaction in excess of 500.

EXAMPLE 5
Synthesis Of Additional Amino Acids

Following essentially the procedures described in Example 4, the synthesis of L-glutamate, L-methionine, and L-norvaline was demonstrated from the sodium salts of the corresponding ketoacids: 2-ketoglutaric acid (50 mM, 252 milligrams), 4-methylthio-2-oxobutyric acid (50 mM, 255 milligrams), and 2-ketovaleric acid (50 mM, 207 milligrams), respectively. In all cases the (S)-transaminase produced exclusively the L-isomer of the amino acid, at concentrations of 45, 47, and 46mM respectively.

What is claimed:

1. In the stereoselective synthesis of a chiral amine in which a ketone is brought into contact with a transaminase in the presence of an amino donor, the carbonyl group of the ketone being bound either to two substituents that differ from each other in structure or chirality or to a divalent group that together with the carbonyl group constitutes a chiral cyclic structure, the improvement which comprises utilizing 2-aminopropane as the amine donor.

2. In the stereoselective synthesis of a chiral amino acid in which a 2-keto-carboxylic acid is brought into contact with a transaminase in the presence of an amino donor, the improvement which comprises utilizing 2-aminopropane as the amine donor.

3. The method of preparing (S)-1-methoxy-2-aminopropane which comprises bringing methoxyacetone into contact with a transaminase in the presence of 2-aminopropane as an amine donor until a substantial amount of methoxyacetone is converted to (S)-1-methoxy-2-aminopropane and 2-aminopropane is converted to acetone, and isolating the (S)-1-methoxy-2-aminopropane.

* * * * *